United States Patent

Omura et al.

Patent Number: 4,575,497
Date of Patent: Mar. 11, 1986

[54] 3, 3″, 4″-TRI-O-ACYLSPIRAMYCIN I

[75] Inventors: Satoshi Omura, Tokyo; Hiroshi Sano, Machida; Kinya Yamashita, Mishima; Ryo Okachi, Sunto, all of Japan

[73] Assignee: Kyowa Hakko Kogyo Co., Ltd, Tokyo, Japan

[21] Appl. No.: 680,347

[22] Filed: Dec. 11, 1984

[30] Foreign Application Priority Data

Dec. 13, 1983 [JP] Japan .................. 58-234761

[51] Int. Cl.$^4$ ...................... A61K 31/71; C07H 17/08
[52] U.S. Cl. ...................... 514/30; 536/7.1; 536/7.4
[58] Field of Search .................. 536/7.1, 7.4; 424/180; 514/30

[56] References Cited

U.S. PATENT DOCUMENTS 4,242,504 10/1980 Sakakibara et al. ................ 536/7.1

OTHER PUBLICATIONS

Takahira, *Chemical Abstracts*, (1971), 74512p, 88896d.

*Primary Examiner*—Johnnie R. Brown
*Assistant Examiner*—Elli Peselev
*Attorney, Agent, or Firm*—Michael N. Meller

[57] ABSTRACT

3, 3″, 4″-Tri-O-acylspiramycin I represented by the formula:

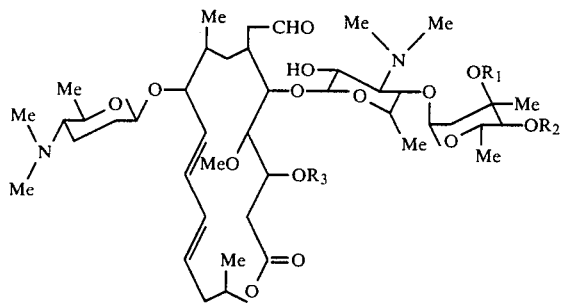

wherein $R_1$, $R_2$ and $R_3$ are the same or different groups, and at least one of the groups is a straight or branched chain alkylcarbonyl group represented by —$COC_mH_{2m+1}$ wherein m is an integer of 2–4 and the other group(s) are straight or branched chain alkylcarbonyl group(s) represented by —$COC_nH_{2n+1}$ wherein n is an integer of 1–4, and its pharmacologically acceptable acid addition salts.

1 Claim, No Drawings

3, 3'', 4''-TRI-O-ACYLSPIRAMYCIN I

BACKGROUND OF THE INVENTION

This invention relates to a novel derivative of the antibiotic spiramycin I, and more particularly to 3, 3'', 4''-tri-O-acylspiramycin I represented by the formula (I):

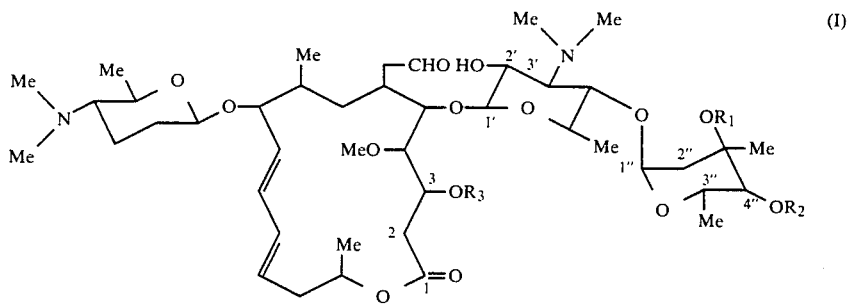

wherein $R_1$, $R_2$ and $R_3$ are the same or different groups, and at least one of the groups is a straight or branched chain alkylcarbonyl group represented by $-COC_mH_{2m+1}$, wherein m is an integer of 2–4, and the other group(s) are straight or branched chain alkylcarbonyl group(s) represented by $-COC_nH_{2n+1}$, wherein n is an integer of 1–4, which will be hereinafter referred to as "Compound (I)", and its pharmacologically acceptable acid addition salts.

Spiramycin is an antibiotic which is classified as a 16-membered, macrolide antibiotic and has a remarkable antibacterial effect on Gram-positive bacteria and mycoplasma. Owing to differences in substituents in the 3-position, spiramycin I (hydroxyl group in the 3-position), spiramycin II (acetyloxy group in the 3-position) and spiramycin III (propionyloxy group in the 3-position) are known as spiramycin.

Heretofore, the O-acetyl derivative of the spiramycin mixture, which is considered as a mixture of the 4''-O-acetyl derivative and the 3'', 4''-di-O-acetyl derivative wherein when the substituent in the 3-position is a hydroxyl group, the hydroxyl group is also acetylated, is known [Chemical Abstracts vol. 75, 88896d, 74512p (1971)]. The O-acetyl derivative of the spiramycin mixture is commonly called "acetylspiramycin", adopted in the Japan Pharmacopoeia X, and widely used for therapeutic purposes. Further, though GB1158396A discloses 3, 3'', 4'''-tri-O-acetylspiramycin I as obtained, it is presumed from the described method for the production that the preparation contains considerable amounts of by-products such as diacetyl derivatives.

Further, it has been known that the 3'', 9-di-O-acetyl compound of midecamycin [J. of Antibiotics 29, 536 (1976)] and the 3''-O-propionyl compound of leucomycin A₅ (Japanese Published Unexamined Patent Application No. 148793/1979) have a better in vivo activity and reduce bitterness, compared with their starting compounds.

SUMMARY OF THE INVENTION

The compounds of the present invention have antibacterial activities and show a minimum inhibitory concentration (MIC) substantially equal to that of spiramycin I. Further, the present compound show better in vivo therapeutic effects than that of spiramycin I and are useful as infection-healing medicaments because the bitterness specific to the macrolide antibiotics can substantially be removed.

The present invention relates to Compound (I) and its pharmacologically acceptable acid addition salts.

Specific examples of Compound (I) include 3, 3''-di-O-acetyl-4''-O-propionylspiramycin I (1); 3, 3''-di-O-acetyl-4''-O-butyrylspiramycin I (2); 3,3''-di-O-propionyl-4''-O-acetylspiramycin I (3); 3, 3'', 4''-tri-O-propionylspiramycin I (4); 3, 4''-di-O-acetyl-3''-O-propionylspiramycin I (5); 3, 4''-di-O-acetyl-3''-O-butyrylspiramycin I (6); 3, 4''-di-O-propionyl-3''-O-butyrylspiramycin I (7); 3''-O-acetyl-3, 4''-di-O-propionylspiramycin I (8); and 3, 3''-di-O-propionyl-4''-O-butyrylspiramycin I (9). The numbers given in parentheses correspond to the compound numbers in the tables which follow. Particularly, compounds of compound numbers 4, 6, 8 and 9 among the abovementioned compounds exhibited a more excellent therapeutic effect than acetylspiramycin and 3, 3'', 4''-tri-O-acetylspiramycin I in an infection-healing test in mice using *Streptococcus pneumoniae* Type III as a test microorganism.

Examples of pharmacologically acceptable acid addition salts of Compound (I) are various inorganic acid addition salts such as hydrochloride, hydrobromide, hydroiodide, nitrate, sulfate and phosphate, and various organic acid addition salts such as formate, acetate, benzoate, maleate, fumarate, succinate, tartrate, citrate, oxalate, glyoxylate, aspartate, methanesulfonate, ethanesulfonate, propanesulfonate, methanedisulfonate, α,β-ethanedisulfonate and benzenesulfonate.

DETAILED DESCRIPTION

Properties of the compounds according to the present invention are as follows:

Structure and physico-chemical properties

The structure of Compound (I) has been determined mainly by nuclear magnetic resonance spectrum (Table I), mass spectrum (Table 2) and other physico-chemical properties (Table 3).

The minimum inhibitory concentration (MIC) of Compound (I) is shown in Table 4 in comparison with that of spiramycin I.

TABLE 1

Carbon nuclear magnetic resonance spectrum

| Carbon No. | Compound No. | | | | | | | | |
|---|---|---|---|---|---|---|---|---|---|
| | 1 | 2 | 3 | 4 | 5 | 6 | 7 | 8 | 9 |
| 1 | 170.0 | 170.1 | 170.0 | 170.0 | 170.1 | 170.0 | 170.1 | 170.0 | 170.1 |
| 2 | 37.1 | 37.2 | 37.3 | 37.3 | 37.2 | 37.1 | 37.4 | 37.4 | 37.4 |
| 3 | 69.1 | 69.2 | 68.8 | 68.8 | 69.2 | 69.1 | 68.8 | 68.9 | 68.9 |
| 4 | 84.7 | 84.7 | 84.7 | 84.7 | 84.8 | 84.7 | 84.7 | 84.8 | 84.8 |
| 5 | 77.5 | 77.4 | 77.9 | 77.7 | 77.9 | 77.9 | 77.7 | 77.9 | 77.8 |
| 6 | 28.6 | 28.7 | 28.7 | 28.8 | 29.3 | 28.7 | 28.8 | 28.9 | 29.1 |
| 7 | 29.9 | 29.9 | 29.9 | 30.0 | 30.0 | 29.9 | 30.0 | 30.0 | 30.1 |
| 8 | 31.7 | 31.8 | 31.7 | 31.7 | 31.9 | 31.8 | 31.7 | 31.8 | 31.9 |
| 9 | 79.6 | 79.6 | 79.5 | 79.5 | 79.8 | 79.7 | 79.6 | 79.5 | 79.6 |
| 10 | 126.4 | 126.5 | 126.5 | 126.5 | 126.6 | 126.4 | 126.6 | 126.7 | 126.7 |
| 11 | 135.4 | 135.5 | 135.3 | 135.3 | 135.5 | 135.5 | 135.4 | 135.3 | 135.4 |
| 12 | 132.3 | 132.3 | 132.2 | 132.2 | 132.3 | 132.3 | 132.2 | 132.3 | 132.3 |
| 13 | 131.8 | 131.8 | 131.9 | 131.8 | 131.9 | 131.8 | 131.9 | 131.8 | 131.9 |
| 14 | 40.9 | 41.0 | 41.0 | 41.0 | 41.1 | 41.0 | 41.0 | 41.1 | 41.1 |
| 15 | 69.1 | 69.2 | 69.1 | 69.1 | 69.2 | 69.1 | 69.1 | 69.3 | 69.2 |
| 16 | 20.3 | 20.4 | 20.3 | 20.3 | 20.4 | 20.3 | 20.3 | 20.4 | 20.4 |
| 17 | 42.3 | 42.3 | 42.3 | 42.3 | 42.3 | 42.3 | 42.3 | 42.4 | 42.5 |
| 18 | 201.2 | 201.2 | 201.2 | 201.2 | 201.2 | 201.2 | 201.2 | 201.2 | 201.3 |
| 19 | 15.2 | 15.3 | 15.2 | 15.2 | 15.3 | 15.2 | 15.3 | 15.3 | 15.4 |
| 20 | 62.5 | 62.6 | 62.5 | 62.5 | 62.6 | 62.5 | 62.5 | 62.5 | 62.5 |
| 1' | 103.5 | 103.6 | 103.5 | 103.5 | 103.5 | 103.4 | 103.5 | 103.8 | 103.7 |
| 2' | 70.4 | 70.4 | 70.5 | 70.5 | 70.5 | 70.4 | 70.5 | 70.6 | 70.7 |
| 3' | 69.1 | 69.2 | 69.1 | 69.1 | 69.2 | 69.1 | 69.1 | 69.2 | 69.2 |
| 4' | 77.4 | 77.4 | 77.3 | 77.3 | 77.5 | 77.2 | 77.3 | 77.4 | 77.3 |
| 5' | 73.1 | 73.1 | 73.1 | 73.1 | 73.1 | 73.1 | 73.1 | 73.2 | 73.2 |
| 6' | 18.2 | 18.3 | 18.2 | 18.2 | 18.3 | 18.2 | 18.2 | 18.3 | 18.3 |
| 3'-N(CH$_3$)$_2$ | 41.5 | 41.5 | 41.5 | 41.5 | 41.5 | 41.5 | 41.5 | 41.6 | 41.6 |
| 1'' | 98.5 | 98.5 | 98.4 | 98.4 | 98.6 | 98.4 | 98.4 | 98.5 | 98.5 |
| 2'' | 36.6 | 36.6 | 36.6 | 36.6 | 36.7 | 36.7 | 36.7 | 36.6 | 36.8 |
| 3'' | 77.9 | 77.9 | 77.6 | 77.7 | 77.7 | 77.6 | 77.7 | 77.6 | 77.8 |
| 4'' | 80.2 | 80.2 | 80.2 | 80.2 | 80.3 | 80.1 | 80.1 | 80.2 | 80.2 |
| 5'' | 63.4 | 63.4 | 63.3 | 63.3 | 63.4 | 63.3 | 63.3 | 63.4 | 63.4 |
| 6'' | 17.3 | 17.3 | 17.3 | 17.3 | 17.4 | 17.3 | 17.3 | 17.4 | 17.4 |
| 7'' | 22.2 | 22.3 | 22.3 | 22.3 | 22.4 | 22.3 | 22.4 | 22.3 | 22.5 |
| 1''' | 100.1 | 100.2 | 100.0 | 99.9 | 100.2 | 100.1 | 100.0 | 100.1 | 100.1 |
| 2''' | 31.2 | 31.3 | 31.2 | 31.2 | 31.2 | 31.1 | 31.3 | 31.3 | 31.3 |
| 3''' | 18.4 | 18.5 | 18.5 | 18.5 | 18.7 | 18.6 | 18.5 | 18.6 | 18.5 |
| 4''' | 64.8 | 64.8 | 64.8 | 64.8 | 64.9 | 64.8 | 64.8 | 65.0 | 65.0 |
| 5''' | 73.7 | 73.8 | 73.7 | 73.7 | 73.7 | 73.6 | 73.7 | 73.9 | 73.9 |
| 6''' | 19.0 | 19.0 | 19.0 | 18.9 | 19.1 | 19.0 | 19.0 | 19.0 | 19.0 |
| 4'''-N(CH$_3$)$_2$ | 40.7 | 40.7 | 40.6 | 40.6 | 40.6 | 40.6 | 40.7 | 40.7 | 40.8 |
| COCH$_3$ | 21.2,22.5 | 21.3,22.5 | 20.8 | | 20.8,21.3 | 20.7,21.2 | | 22.5 | |
| COCH$_3$ | 170.4,170.8 | 170.4,170.8 | 170.5 | | 170.6,170.8 | 170.5,170.8 | | 170.4 | |
| COCH$_2$CH$_3$ | 9.3 | | 9.0,9.1 | 8.9,9.1,9.2 | 9.2 | | 9.0,9.3 | 9.0,9.3 | 9.0,9.2 |
| COCH$_2$CH$_3$ | 27.5 | | 27.6,28.7 | 27.5(2),28.7 | 28.8 | | 27.6(2) | 27.6(2) | 27.7,28.8 |
| COCH$_2$CH$_3$ | 174.0 | | 173.7,173.8 | 173.6,173.8 173.9 | 173.7 | | 173.9,174.0 | 173.8,174.0 | 173.7,173.8 |
| COCH$_2$CH$_2$CH$_3$ | | 13.7 | | | | 13.8 | 13.8 | | 13.7 |
| COCH$_2$CH$_2$CH$_3$ | | 18.5 | | | | 18.2 | 18.2 | | 18.5 |
| COCH$_2$CH$_2$CH$_3$ | | 36.1 | | | | 37.3 | 37.4 | | 36.2 |
| COCH$_2$CH$_2$CH$_3$ | | 173.2 | | | | 172.8 | 172.8 | | 173.2 |

TABLE 2

Fragments in mass spectrum
$M^+$: 1

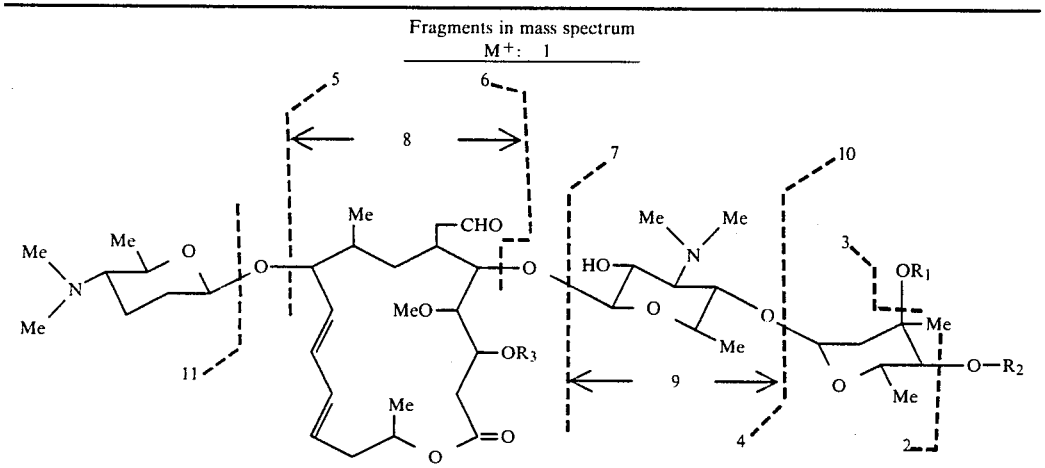

| Fragment | | Compound No. 1 | 2 | 3 | 4 | 5 | 6 | 7 | 8 | 9 |
|---|---|---|---|---|---|---|---|---|---|---|
| 1 | | +H983 | 996 | +H997 | — | 982 | 996 | 1024 | +H997 | 1024 |
| 2 | | 910 | −H909 | −H923 | — | −H923 | 937 | +H952 | −2H922 | 951 |
| 3 | | +H924 | — | — | — | +H910 | 909 | — | — | 937 |
| 4 | +H | 740 | — | — | — | 740 | — | — | 755 | — |
| 5 | | +H825 | — | — | +H853 | +H825 | +H839 | 866 | — | −H864 |
| 6 | | 555 | — | — | — | — | — | — | — | 564 |
| 7 | | 416 | 430 | 416 | +H431 | 416 | 430 | 444 | +H417 | 444 |
| 8 | −H | 391 | — | 405 | — | 391 | — | 405 | — | 405 |
| 9 | | +H174 | 173 | +H174 | 173 | 173 | +H174 | +H174 | +H174 | +H174 |
| 10 | | 243 | 257 | 243 | 257 | 243 | 257 | 271 | 243 | 271 |
| 11 | | 142 | 142 | 142 | 142 | 142 | 142 | 142 | 142 | 142 |

TABLE 3

Physico-chemical properties

| Compound No. | TLC Rf value | $[\alpha]_D^{19}$ | UV spectrum $\lambda_{max}^{MeOH}$ ($\epsilon$) |
|---|---|---|---|
| 1 | 0.45 | −54 | 231 nm (24,400) |
| 2 | 0.46 | −59 | 231 nm (22,000) |
| 3 | 0.46 | −66 | 232 nm (29,500) |
| 4 | 0.51 | −85.3 | 231 nm (22,500) |
| 5 | 0.43 | −62.6 | 234 nm (35,300) |
| 6 | 0.44 | −58.2 | 231 nm (24,500) |
| 7 | 0.50 | −51.2 | 235 nm (22,500) |
| 8 | 0.57 | −62.6 | 239 nm (38,600) |
| 9 | 0.57 | −61.0 | 233 nm (37,700) |

TLC: Merck Kiesel gel 60 [developing solvent (chloroform:methanol:concentrated ammonia = 10:1:0.01]

TABLE 4

Minimum inhibitory concentration (MIC, μg/ml)

| Compound No. | A | B | C | D | E | F | G |
|---|---|---|---|---|---|---|---|
| 1 | 3.12 | >100 | 1.56 | 3.12 | <0.1 | >100 | >100 |
| 2 | 1.56 | >100 | 1.56 | 1.56 | <0.1 | >100 | 100 |
| 3 | 3.12 | >100 | 3.12 | 3.12 | <0.1 | >100 | >100 |
| 4 | 1.56 | >100 | 1.56 | 1.56 | <0.1 | >100 | >100 |
| 5 | 3.12 | >100 | 3.12 | 1.56 | <0.1 | >100 | >100 |
| 6 | 6.25 | >100 | 3.12 | 1.56 | 0.2 | >100 | >100 |
| 7 | 3.12 | >100 | 1.56 | 1.56 | <0.1 | >100 | >100 |
| 8 | 3.12 | >100 | 3.12 | 3.12 | 0.2 | >100 | >100 |
| 9 | 3.12 | >100 | 3.12 | 3.12 | 0.2 | >100 | >100 |

TABLE 4-continued

Minimum inhibitory concentration (MIC, μg/ml)

| Compound No. | A | B | C | D | E | F | G |
|---|---|---|---|---|---|---|---|
| SPMI | 1.56 | >100 | 0.78 | 1.56 | <0.1 | 100 | 100 |

Remark: medium used: Heart infusion agar (pH 7.0)
A: *Staphylococcus aureus* KB210
B: *Staphylococcus aureus* KB199
C: *Bacillus subtilis* KB211
D: *Bacillus cereus* KB143
E: *Micrococcus ruteus* KB212
F: *Escherichia coli* KB213
G: *Klebsiella pneumoniae* KB214
SPMI: Spiramycin I A test example of the therapeutic effect of Compound (I) in experimental test mice protection test will be given below:

Test Example

Animal: ddY-strain male mice, 19±1g, one group consisting of ten mice.

Test bacterium: *Streptococcus pneumoniae* Type III, Inoculation rate: $1.1 \times 10^2$ cfu/mouse.

The predetermined amount of the precultured test bacteria was inoculated via i.p.

Medicament administration: 60 mg/kg of each of the medicaments was suspended in 0.3% CMC, and orally administered just after the inoculation of bacteria.

The number of survived animals on the 7th day is shown in Table 5.

TABLE 5

Infection-healing effect

| Compound No. | 1 | 2 | 3 | 4 | 5 | 6 | 7 | 8 | 9 | AcSPM | SPMI |
|---|---|---|---|---|---|---|---|---|---|---|---|
| Number of survived | 5 | 5 | 5 | 10 | 3 | 10 | 5 | 10 | 8 | 6 | 0 |

TABLE 5-continued

| | Infection-healing effect | | | | | | | | | | |
|---|---|---|---|---|---|---|---|---|---|---|---|
| Compound No. | 1 | 2 | 3 | 4 | 5 | 6 | 7 | 8 | 9 | AcSPM | SPMI |
| mice out of 10 mice | | | | | | | | | | | |

AcSPM: acetylspiramycin

Procedure for producing compound (I)

Compound (I) can be produced by the three steps shown in Table 6, that is, by each of (1) acylation ($R_1$) of hydroxyl groups at the 2'- and 4"-positions or hydroxyl groups at the 3-, 2'-, and 4"-positions, [production of Compound (II)], (2) acylation ($R_2$) of the hydroxyl group at the 4"-position or hydroxyl groups at the 4"- and 3-positions together with a migration reaction of the acyl group ($R_1$) at the 4"-position to hydroxyl group at 3"-position [production of Compound (III)], and (3) removal of the acyl group at the 2'-position [production of Compound (I)].

Spiramycin I has, in total, 4 hydroxyl groups at the 2'-, 3"-, 4"- and 3-positions in the structure.

The reactivity of these hydroxyl groups to acylation under basic conditions is generally in the order of 2'>4">3>3". The desired acyl groups can be introduced on the hydroxyl groups at the 2'- and 4"-positions or on the hydroxyl groups at the 3-, 2'- and 4"-positions by setting appropriate reaction conditions in view of the differences in reactivity. The hydroxyl group at the 3"-position of spiramycin I is considerably low in reactivity and is hardly susceptible to direct acylation according to the ordinary acylation procedure. An acyl group can be introduced at the 3"-position while migrating the acyl group introduced beforehand at the 4"-position to the 3"-position and introducing a new acyl group at the 4"-position. Such migration reaction of the acyl group is well known in sugar chemistry. When a spiramycin I derivative, whose hydroxyl group at the 3-position or 2'-position is free, is used as the starting compound, acyl groups can also be introduced at these positions at the same time. In this manner, a tetraacyl derivative of spiramycin I represented by formula (III), which has the same or different acyl groups at the 3-, 2'-, 3"- and 4"-positions, can be obtained.

Compound (III) can also be produced by acylating 3", 4"-di-O-acylspiramycin I disclosed in Japanese Published Unexamined Patent Application No. 136589/1983 in a similar manner.

Then, the present compound, 3, 3", 4"-tri-O-acyl-spiramycin I can be produced by selective removal of the acyl group at the 2'-position.

TABLE 6

Production procedure

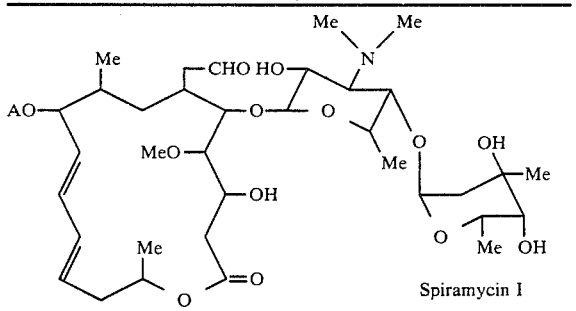

Spiramycin I

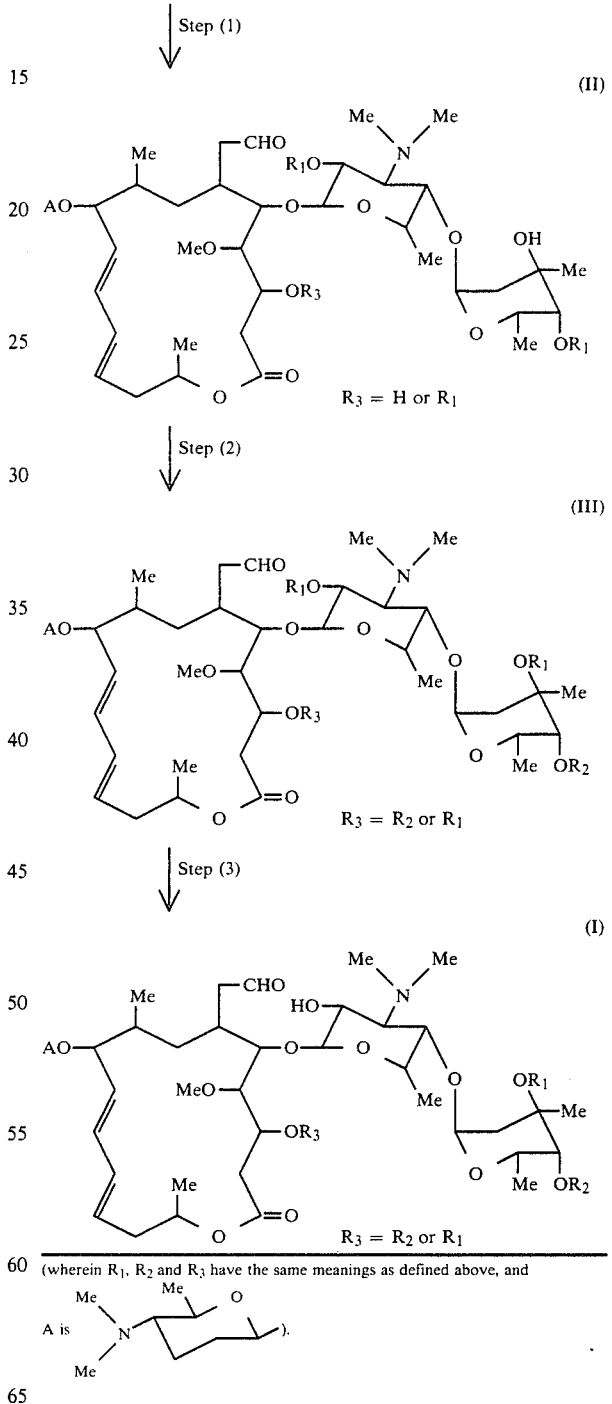

(wherein $R_1$, $R_2$ and $R_3$ have the same meanings as defined above, and

A is 
$\begin{matrix} Me & Me \\ \diagdown & \diagup \\ & N \\ & | \\ & Me \end{matrix}$ ).

Each production step will be described in detail below:

Step (1): Production of Compound (II)

2', 4"-di-O-acylspiramycin I or 3, 2', 4"-tri-O-acylspiramycin I represented by Compound (II) can be produced by the reaction of spiramycin I with an acyl halide or acid anhydride of a carboxylic acid represented by the formula $C_mH_{2m+1}CO_2H$ (wherein m has the same meaning as defined above) or with an acyl halide or acid anhydride of a carboxylic acid represented by the formula $C_nH_{2n+1}CO_2H$ (wherein n has the same meaning as defined above) in the presence of a base in an organic solvent having no active hydrogen atom at 10°–120° C. for 6 hours to 20 days. The organic solvent having no active hydrogen atom is exemplified by chloroform, dichloromethane, dichloroethane, trichloroethane, benzene, toluene, acetone, ethyl acetate, dioxane, tetrahydrofuran, dimethylformamide, etc., preferably, chloroform or dichloromethane. The base is exemplified by pyridine, quinoline, triethylamine, sodium carbonate, potassium carbonate, preferably, pyridine. When pyridine is used as a base, it is possible to dispense with the organic solvent having no active hydrogen.

The acyl halide and carboxylic acid anhydride are exemplified by the acid chlorides, acid bromides and acid anhydrides of acetic acid, propionic acid, butyric acid, valeric acid and isovaleric acid.

When the reaction is carried out with 5 to 20 molar equivalent of an acid anhydride or acyl halide in pyridine-chloroform or -dichloromethane, or in pyridine, at 10°–30° C. for 6 hours to 12 days, 2', 4"-di-O-acyl compound is predominantly obtained. When the reaction is carried out with 15 to 40 molar equivalent of an acid anhydride or acyl halide in pyridine at 30°–120° C. for 5–20 days, 3, 2', 4"-tri-O-acyl compound is predominantly obtained. In either case, the products can be separated and purified by silica gel column chromatography.

Step (2): Production of Compound (III)

Compound (III) can be produced by reacting compound (II) with an acyl halide or an acid anhydride of a carboxylic acid represented by the formula $C_nH_{2n+1}CO_2H$ (wherein n has the same meaning as defined above) when using an acyl halide or an acid anhydride of a carboxylic acid represented by the formula $C_mH_{2m+1}CO_2H$ in the above step (1), or with an acyl halide or an acid anhydride of a carboxylic acid represented by the formula $C_mH_{2m+1}CO_2H$ (wherein m has the same meaning as defined above) when using an acyl halide or an acid anhydride of a carboxylic acid represented by the formula $C_nH_{2n+1}CO_2H$ in the above step (1) in the presence of a base in an organic solvent having no active hydrogen atom at 25°–150° C. for 24 hours to 6 days. The organic solvent having no active hydrogen atom is exemplified by chloroform, dichloromethane, dichloroethane, trichloroethane, benzene, toluene, acetone, ethyl acetate, dioxane, tetrahydrofuran, dimethylformamide, etc., preferably chloroform. The base is exemplified by pyridine, dimethylaminopyridine, quinoline, triethylamine, tribenzylamine, sodium carbonate, potassium carbonate, sodium hydroxide, potassium hydroxide, etc., preferably, pyridine, dimethylaminopyridine and triethylamine, or their combinations.

When pyridine is used as the base, it is possible to dispense with the organic solvent having no active hydrogen.

The acyl halide and carboxylic acid anhydride are exemplified by acid chlorides, acid bromides and acid anhydrides of acetic acid, propionic acid, butyric acid, valeric acid, and isovaleric acid.

It is the most preferable condition to subject Compound (II) to reflux with 20 to 40 molar equivalent of an acid anhydride in chloroform containing triethylamine and dimethylaminopyridine with heating for 40–100 hours, or to subject Compound (II) to reaction with 20 to 40 molar equivalent of an acid anhydride in pyridine containing dimethylaminopyridine at 70°–115° C. for 40–150 hours. In either case, the yield is considerably lowered, when dimethylaminopyridine is dispensed with.

This step is also applicable to the production of 3", 4"-di-O-acylspiramycin I disclosed in Japanese Patent Application No. 136589/1983 and The Journal of Antibiotics vol. 37, No. 7, pp. 760-772 (1984), where an acyl group can be selected for $R_3$, irrespective of the species of $R_1$ and $R_2$ in Compound (III).

The reaction product can be introduced into the successive step for removing the protective group without any purification, but it can be purified, if required, by silica gel column chromatography.

Step (3): Production of Compound (I)

Compound (I) can be produced by removing the 2'-O-acyl group (partly 18-enolacyl group) of Compound (III). That is, Compound (I) can be obtained by dissolving Compound (III) in an alcohol or water-containing organic solvent, and subjecting the solution to reaction at 20°–100° C.

Methanol, ethanol, etc. can be used as the alcohol, and mixtures of methanol, ethanol, acetone, 2-methoxyethanol, ethylene glycol, ethylene glycol dimethyl ether, tetrahydrofuran, dioxane, dimethylformamide, etc. with water can be used as the water-containing organic solvent. Particularly, water-containing methanol is preferable. The reaction product is purified by silica gel column chromatography to obtain pure Compound (I).

Examples will be given below:

EXAMPLE 1

Production of 3, 3"-di-O-acetyl-4"-O-propionylspiramycin I (1-1)

Production of 3, 2', 4"-tri-O-acetylspiramycin I:

First, 5.05 g of spiramycin I as vacuum-dried at 60° C. for 3 hours is dissolved in 60 ml of pyridine, and 6 ml of acetic anhydride is added thereto with ice cooling and stirring. Then, the temperature of the mixture is brought back to room temperature and the mixture is allowed to stand. After 6 days, 3 ml of acetic anhydride is further added thereto, and the mixture is heated at 50° C. for 5 days. Then, 10 ml of methanol is added to the reaction mixture, and the mixture is allowed to stand for one hour. Then, the mixture is diluted with 500 ml of chloroform, and washed with 500 ml of water. The chloroform solution is dried over sodium sulfate, and then concentrated under reduced pressure. The thus obtained brown glass-like substance is purified by silica gel column chromatography using benzene:acetone=5:2 as a developing solvent system, whereby 636 mg of the captioned compound can be obtained in a colorless, glass-like state (11.0%). TLC Rf value: 0.88 (chloroform:methanol:concentrated ammonia water=10:1:0.01), $[\alpha]_D^{19}$ −93.6° (c 1, chloroform).

(1-2) Production of captioned compound:

First, 920 mg of 3, 2', 4"-tri-O-acetylspiramycin I and 98 mg of N, N-dimethylaminopyridine are dissolved in 25 ml of chloroform, and then 3.2 ml of triethylamine and subsequently, 3.2 ml of propionic anhydride are added thereto. The mixture is gently heated and refluxed.

After 98 hours, the temperature of the reaction mixture is brought back to room temperature, and then 5 ml of methanol is added thereto. The mixture is allowed to stand at room temperature for one hour. The reaction mixture is diluted with 90 ml of ethyl acetate and washed with 90 ml of an aqueous saturated sodium hydrogen carbonate solution and then with 90 ml of water. The ethyl acetate solution is dried over sodium sulfate and concentrated under reduced pressure, whereby a brown solid is obtained.

The solid is dissolved in 45 ml of 70% aqueous methanol and the solution is heated at 50° C. for 62 hours. The reaction solution is diluted with 70 ml of chloroform, and washed with 90 ml of water, and concentrated under reduced pressure, whereby a brown, glass-like substance is obtained. The thus obtained, glass-like substance is purified by silica gel column chromatography, using benzene:acetone=4:1 as a developing solvent system, whereby 387 mg. of the captioned compound can be obtained as a colorless powder (41.4%). The physico-chemical properties of the substance are shown in Tables 1–3.

EXAMPLE 2

Production of 3, 3″-di-O-acetyl-4″-O-butyrylspiramycin I

First, 1.00 g of 3, 2″, 4″-tri-O-acetylspiramycin I produced according to Example (1-1) and 107 mg of N, N-dimethylaminopyridine are dissolved in 27 ml of chloroform, and then 3.4 ml of triethylamine and subsequently 4.3 ml of butyric anhydride are added thereto. The mixture is gently heated and refluxed. After 89 hours, the temperature of the reaction solution is brought back to room temperature, and then 5 ml of methanol is added thereto. The mixture is allowed to stand at room temperature for one hour. The reaction solution is diluted with 100 ml of ethyl acetate, and washed with 100 ml of an aqueous saturated sodium hydrogen carbonate solution and then with 100 ml of water. The ethyl acetate solution is dried over sodium sulfate, and concentrated under reduced pressure, whereby a brown solid is obtained.

The solid is dissolved in 49 ml of 70% aqueous methanol and the solution is heated at 50° C. for 86 hours. The reaction solution is diluted with 70 ml of chloroform, washed with 90 ml of water, and concentrated under reduced pressure, whereby a brown, glass-like substance is obtained.

The thus obtained, glass-like substance is purified by silica gel chromatography, using benzene:acetone =4:1 as a developing solvent system, whereby 327 mg of the captioned compound is obtained as a colorless power (31.8%). The physico-chemical properties of the compound are shown in Tables 1–3.

EXAMPLE 3

Production of 3, 3″-di-O-propionyl-4″-O-acetylspiramycin I (3-1) Production of 3, 2′, 4″-tri-O-propionylspiramycin I:

First, 5.05 g of spiramycin I as vacuum-dried at 60° C. for 3 hours is dissolved in 76 ml of pyridine, and 12 ml of propionic anhydride is added thereto with ice ccoling and stirring. The reaction mixture is heated at 50° C. for 7 days, and then 7.5 ml of water is added thereto. The mixture is allowed to stand at room temperature for one hour. The reaction mixture is diluted with 500 ml of chloroform and washed with 500 ml of water. The chloroform solution is dried over sodium sulfate, and concentrated under reduced pressure. The thus obtained, brown, glass-like substance is purified by silica gel column chromatography, using benzene:acetone =3:1 as a developing solvent system, whereby 1.40 g of the captioned substance is obtained in a colorless glass-like state (23.1%). TLC (Kiesel gel 60 is used, and will hereinafter be used). Rf value: 0.89 (chloroform:methanol:concentrated ammonia water=10:1:0.01), $[\alpha]_D^{19}$ −85.8° C. (c 1, chloroform)

(3-2) Production of captioned compound:

First, 940 mg of 3, 2′, 4″-tri-O-propionylspiramycin I and 95 mg of N, N-dimethylaminopyridine are dissolved in 26 ml of chloroform, and then 3.3 ml of triethylamine and subsequently, 2.5 ml of acetic anhydride are added thereto. Then, the mixture is gently heated and refluxed. After 164 hours, the temperature of the reaction solution is brought back to room temperature and 5 ml of methanol is added thereto. The mixture is allowed to stand at room temperature for one hour. Then, the reaction mixture is diluted with 100 ml of ethyl acetate, and washed with 100 ml of an aqueous saturated sodium hydrogen carbonate solution and then with 100 ml of water. Then, the ethyl acetate solution is dried over sodium sulfate and concentrated under reduced pressure, whereby a brown solid is obtained.

The solid is dissolved in 49 ml of 70% aqueous methanol and the solution is heated at 50° C. for 56 hours. The reaction solution is diluted with 70 ml of chloroform, washed with 90 ml of water and concentrated under reduced pressure, whereby a brown, glass-like substance is obtained. The thus obtained glass-like substance is purified by silica gel column chromatography, using benzene:acetone=5:1as a developing solvent system, whereby 140 mg of the captioned compound is obtained as a colorless powder (15.1%). The physico-chemical properties of the substance are shown in Tables 1–3.

EXAMPLE 4

Production of 3, 3″, 4″-tri-O-propionylspiramycin I (4-1) Production of 2′, 4″-di-O-propionylspiramycin I:

First, 5.05 g of spiramycin I as vacuum-dried at 60° C. for 3 hours is dissolved in 60 ml of chloroform, and then 9.5 ml of pyridine and subsequently, 7.8 ml of propionic anhydride are added thereto with ice cooling and stirring. Then, the temperature of the mixture is brought back to room temperature and the mixture is allowed to stand. After 4 days, 4.8 ml of pyridine and 3.9 ml of propionic anhydride are further added thereto, and the mixture is allowed to stand at room temperature. After 6 days, 20 ml of methanol is added to the reaction mixture, and the mixture is allowed to stand for one hour, diluted with 400 ml of chloroform, and washed with 450 ml of water. The chloroform solution is dried over sodium sulfate and concentrated under reduced pressure. The thus obtained brown, glass-like substance is purified by silica gel column chromatography, using benzene:acetone=5:2 as a developing solvent system, whereby 3.13 g of the captioned substance can be obtained in a colorless glass-like state (54.7%). TLC Rf value: 0.49 (chloroform:methanol:concentrated ammonia water=10:1:0.01), $[\alpha]_D^{19}$ −88° (c 1, chloroform).

(4-2) Production of the captioned compound:

First, 1.00 g of 2', 4"-di-O-propionylspiramycin I and 103 mg of N, N-dimethylaminopyridine are dissolved in 27 ml of chloroform, and then 3.5 ml of triethylamine and subsequently, 3.4 ml of propionic anhydride are added thereto. The mixture is gently heated and refluxed.

After 84 hours, the temperature of the reaction solution is brought back to room temperature, and then 5 ml of methanol is added thereto. The mixture is allowed to stand at room temperature for one hour. The reaction mixture is diluted with 100 ml of ethyl acetate, and washed with 100 ml of an aqueous saturated sodium hydrogen carbonate solution and then with 100 ml of water. The ethyl acetate solution is dried over sodium sulfate and concentrated under reduced pressure, whereby a brown solid is obtained.

The solid is dissolved in 49 ml of 70% aqueous methanol and the solution is heated at 50° C. for 120 hours. The reaction solution is diluted with 70 ml of chloroform, washed with 90 ml of water and concentrated under reduced pressure, whereby a brown, glass-like substance is obtained. The thus obtained glass-like substance is purified by silica gel column chromatography, using benzene:acetone=4:1 as a developing solvent system, whereby 300 mg of the captioned compound is obtained as a colorless powder (28.3%). The physico-chemical properties of the substance are shown in Tables 1-3.

EXAMPLE 5

Production of 3, 4"-di-O-acetyl-3"-O-propionylspiramycin I

First, 1.00 g of 2', 4"-di-O-propionylspiramycin I produced according to Example (4-1) and 103 mg of N, N-dimethylaminopyridine are dissolved in 27 ml of chloroform, and 3.5 ml of triethylamine and then 2.7 ml of acetic anhydride are added thereto. The mixture is gently heated and refluxed.

After 60 hours, the temperature of the reaction solution is brought back to room temperature, and then 5 ml of methanol is added thereto The mixture is allowed to stand at room temperature for one hour. Then, the reaction mixture is diluted with 100 ml of ethyl acetate and washed with 100 ml of a saturated aqueous sodium hydrogen carbonate solution and then with 100 ml of water. The ethyl acetate solution is dried over sodium sulfate and concentrated under reduced pressure, whereby a brown solid is obtained.

The solid is dissolved in 49 ml of 70% aqueous methanol, and the solution is heated at 50° C. for 98 hours. The reaction solution is diluted with 70 ml of chloroform, washed with 90 ml of water, and concentrated under reduced pressure, whereby a brown, glass-like substance is obtained.

The thus obtained glass-like substance is purified by silica gel column chromatography, using benzene:acetone=5:1 as a developing solvent system, whereby 370 mg of the captioned compound is obtained as a colorless powder (35.8%). The physico-chemical properties of the substance are shown in Tables 1-3.

EXAMPLE 6

Production of 3, 4"-di-O-acetyl-3"-O-butyrylspiramycin I (6-1) Production of 2', 4"-di-O-butyrylspiramycin I:

First, 5.05 g of spiramycin I as vacuum-dried at 60° C. for 3 hours is dissolved in 60 ml of chloroform, and 9.5 ml of pyridine and then 9.5 ml of butyric anhydride are added thereto with ice cooling and stirring. The temperature of the mixture is brought back to room temperature and then, the mixture is allowed to stand. After 2 days, 4.8 ml of pyridine and 4.8 ml of butyric anhydride are added thereto. After 8 days 4.8 ml of pyridine and 4.8 ml of butyric anhydride are further added thereto, and the mixture is allowed to stand at room temperature. After 9 days, 20 ml of methanol is added to the reaction mixture and the mixture is allowed to stand for one hour. Then, the mixture is diluted with 400 ml of chloroform and washed with 450 ml of water. The chloroform solution is dried over sodium sulfate, and concentrated under reduced pressure, and the thus obtained, brown, glass-like substance is purified by silica gel column chromatography, using benzene:acetone=5:2 as a developing solvent system, whereby 3.26g of the captioned substance is obtained in a colorless glass-like state (55.3%). TLC Rf value: 0.46 (chloroform:methanol:concentrated ammonia water=10:1:0.01), $[\alpha]_D^{19}$ −91° (c 1, chloroform).

(6-2) Production of the captioned compound:

First, 1.00 g of 2', 4"-di-O-butyrylspiramycin I and 108 mg of N, N-dimethylaminopyridine are dissolved in 27 ml of chloroform, and then 3.5 ml of triethylamine and subsequently 2.8 ml of acetic anhydride are added thereto. Then, the mixture is gently heated and refluxed. After 75 hours, the temperature of the reaction solution is brought back to room temperature, and then 5 ml of methanol is added thereto. The mixture is allowed to stand at room temperature for one hour. The reaction solution is diluted with 100 ml of ethyl acetate and washed with 100 ml of a saturated aqueous sodium hydrogen carbonate solution and then with 100 ml of water. The ethyl acetate solution is dried over sodium sulfate and concentrated under reduced pressure, whereby a brown solid is obtained.

The solid is dissolved in 49 ml of 70% aqueous methanol, and the solution is heated at 50° C. for 67 hours. The reaction solution is diluted with 70 ml of chloroform, washed with 90 ml of water and concentrated under reduced pressure, whereby a brown, glass-like substance is obtained. The thus obtained glass-like substance is purified by silica gel column chromatography, using benzene:acetone=3:1 as a developing solvent system, whereby 450 mg of the captioned compound is obtained as a colorless powder (44.3%). The physico-chemical properties of the substance are shown in Tables 1-3.

EXAMPLE 7

Production of 3, 4"-di-O-propionyl-3"-O-butyrylspiramycin I

First, 1.00 g of 2', 4"-di-O-butyrylspiramycin I produced according to Example (6-1) and 108 mg of N, N-dimethylaminopyridine are dissolved in 49 ml of chloroform and then 3.5 ml of triethylamine and subsequently 3.6 ml of propionic anhydride are added thereto. The mixture is gently heated and refluxed. After 97 hours, the temperature of the reaction solution is brought back to room temperature, and 5 ml of methanol is added thereto. The mixture is allowed to stand at room temperature for one hour. The reaction mixture is diluted with 100 ml of ethyl acetate, and washed with 100 ml of a saturated aqueous sodium hydrogen carbonate solution and then with 100 ml of water. The ethyl acetate solution is dried over sodium sulfate, and concentrated under reduced pressure, whereby a brown solid is obtained.

The solid is dissolved in 49 ml of 70% aqueous methanol and the solution is heated at 50° C. for 44 hours. The reaction solution is diluted with 70 ml of chloroform, washed with 90 ml of water, and concentrated under reduced pressure, whereby a brown, glass-like substance is obtained. The thus obtained, glass-like substance is purified by silica gel column chromatography, using benzene:acetone=5:1 as a developing solvent system, whereby 308 mg of the captioned compound is obtained as a colorless powder (29.5%). The physico-chemical properties of the substance are shown in Tables 1-3.

EXAMPLE 8

Production of 3″-O-acetyl-3, 4″-di-O-propionylspiramycin I (8-1) Production of 2′, 4″-di-O-acetylspiramycin I:

First, 2.00 g of spiramycin I as vacuum-dried at 60° C. for 3 hours is dissolved in 30 ml of pyridine, and 2.4 ml of acetic anhydride is added thereto with ice cooling and stirring. The temperature of the reaction mixture is brought back to room temperature and then, the mixture is allowed to stand for 20 hours at room temperature. Then, 8 ml of methanol is added thereto and the mixture is allowed to stand for one hour. Then, the mixture is diluted with 100 ml of chloroform and washed with 100 ml of a saturated aqueous sodium hydrogen carbonate solution and then with 100 ml of water. The chloroform solution is dried over sodium sulfate, and concentrated under reduced pressure. The resulting brown powder is purified by silica gel column chromatography, using benzene:acetone=3:1-2:1 (the ratio being gradually changed) as a developing solvent system, whereby 1.02 g of the captioned compound is obtained as a colorless powder (46.3%). TLC Rf value:0.51 (chloroform:methanol:concentrated ammonia water=10:1:0.01), $[\alpha]_D^{19}$ −88.1° (c 1.0, chloroform).

(8-2) Production of the captioned compound:

First, 1.02g of 2′, 4″-di-O-acetylspiramycin I and 113 mg of N, N-dimethylaminopyridine are dissolved in 27 ml of chloroform, and 3.5 ml of triethylamine and then 3.7 ml of propionic anhydride are added thereto. The mixture is gently heated under reflux. After 74 hours, the temperature of the reaction solution is brought back to room temperature, 5 ml of methanol is added thereto and the mixture is allowed to stand for one hour. The reaction mixture is diluted with 100 ml of ethyl acetate, and washed with 100 ml of a saturated aqueous sodium hydrogen carbonate solution and then with 100 ml of water. The ethyl acetate solution is dried over sodium sulfate and concentrated under reduced pressure to obtain a brown powder.

The powder is dissolved in 49 ml of 70% aqueous methanol and the solution is heated at 50° C. for 96 hours. The reaction mixture is diluted with 70 ml of chloroform, washed with 70 ml of water and concentrated under reduced pressure to obtain a brown glass-like substance. The glass-like substance is purified by silica gel column chromatography, using chloroform:methanol:concentrated ammonia water=50:1:0.01 as a developing solvent system, whereby 419 mg of the captioned compound is obtained as a colorless powder (38.9%). The physico-chemical properties of the substance are shown in Tables 1-3.

EXAMPLE 9

Production of 3, 3″-di-O-propionyl-4″-O-butyrylspiramycin I

First, 693 mg of 3, 2′, 4″-tri-O-propionylspiramycin I produced according to Example (3-1) and 74 mg of N, N-dimethylaminopyridine are dissolved in 19 ml of chloroform, 2.4 ml of triethylamine and then 3.0 ml of acetic anhydride are added thereto, and the mixture is gently heated under reflux. After 48 hours, the temperature of the reaction mixture is brought back to room temperature, 5 ml of methanol is added thereto and the mixture is allowed to stand for one hour. The reaction mixture is diluted with 70 ml of ethyl acetate and washed with 70 ml of a saturated aqueous sodium hydrogen carbonate solution and then with 70 ml of water. The ethyl acetate solution is dried over sodium sulfate and concentrated under reduced pressure to obtain a brown solid.

The solid is dissolved in 34 ml of 70% aqueous methanol and the solution is heated at 50° C. for 50 hours. The temperature of the reaction solution is brought back to room temperature and the solution is diluted with 70 ml of chloroform and washed with 70 ml of water. The chloroform solution is dried over sodium sulfate and concentrated under reduced pressure to obtain a brown glass-like substance. The substance is purified by silica gel chromatography, using chloroform:methanol:concentrated ammonia water=50:1:0.01 as a developing solvent system, whereby 221 mg of the captioned compound is obtained as a colorless powder (31.5%). The physico-chemical properties of the substance are shown in Tables 1-3.

REFERENCE EXAMPLE 1

Comparison of healing effects of acetylspiramycin and 3, 3″, 4″-tri-O-acetylspiramycin I on test infection in mice Animal : ddY-strain male mice, 19±1g, one group consisting of ten mice.

Test bacterium : *Streptococcus pneumoniae* Type III. Inoculation rate : $1.1 \times 10^2$ cfu/mouse.

The predetermined amount of the precultured test bacteria was inoculated via i.p..

Medicament administration : Each of the medicaments was suspended in 0.3% CMC, and orally administered just after the inoculation of bacteria.

ED$_{50}$ values of acetylspiramycin and 3, 3″, 4″-tri-O-acetylspiramycin calculated according to the Probit method based on number of survived animals on the 7th day were almost the same, being 71.1 mg/kg and 69.5 mg/kg respectively.

We claim:

1. 3,3″, 4″-Tri-O-acylspiramycin I represented by the formula:

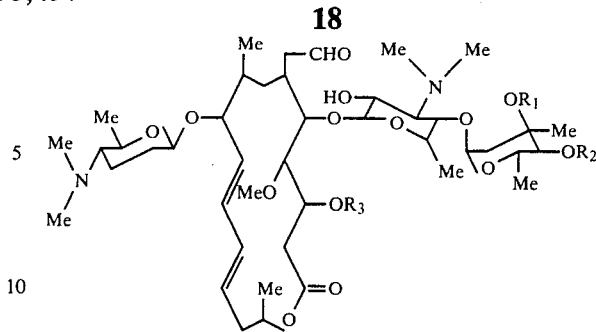
wherein $R_1$, $R_2$ and $R_3$ have the meanings represented by one combination selected from the following (1) to (4) combinations:
|     | $R_1$     | $R_2$     | $R_3$     |
|-----|-----------|-----------|-----------|
| (1) | propionyl | propionyl | propionyl |
| (2) | butyryl   | acetyl    | acetyl    |
| (3) | acetyl    | propionyl | propionyl |
| (4) | propionyl | butyryl   | propionyl.|
* * * * *